United States Patent [19]

Wood

[11] Patent Number: 5,138,890
[45] Date of Patent: Aug. 18, 1992

[54] MULTIPLE SAMPLER ARRAY AND A METHOD

[75] Inventor: Richard F. Wood, Miami, Fla.

[73] Assignee: General Oceanics, Inc., Miami, Fla.

[21] Appl. No.: 576,271

[22] Filed: Aug. 31, 1990

[51] Int. Cl.$^5$ .............................................. G01N 1/12
[52] U.S. Cl. ................................. 73/864.66; 73/864.63
[58] Field of Search ........... 73/864.67, 864.66, 864.63; 33/717

[56] References Cited

U.S. PATENT DOCUMENTS

| | | | |
|---|---|---|---|
| 1,838,729 | 12/1931 | Andrews | 73/864.63 |
| 2,314,372 | 3/1943 | Spilhaus | 73/864.63 X |
| 3,242,740 | 3/1960 | Niskin | 73/864.67 X |
| 3,489,012 | 1/1970 | Niskin | 74/2 X |
| 3,815,422 | 6/1974 | Niskin | 73/864.67 |
| 4,037,477 | 7/1977 | Niskin | 73/864.67 X |
| 4,091,676 | 5/1978 | Niskin | 73/864.67 |
| 4,302,974 | 12/1981 | Niskin | 73/864.62 |
| 4,593,570 | 6/1986 | Niskin | 73/864.67 |
| 4,744,256 | 5/1988 | Niskin | 73/864.66 |
| 4,852,413 | 8/1989 | Niskin | 73/864.67 |

FOREIGN PATENT DOCUMENTS

| | | | |
|---|---|---|---|
| 197638 | 6/1967 | U.S.S.R. | 73/864.66 |
| 763722 | 9/1980 | U.S.S.R. | 73/864.67 |
| 785677 | 12/1980 | U.S.S.R. | 73/864.63 |

Primary Examiner—Tom Noland
Attorney, Agent, or Firm—Jack E. Dominik

[57] ABSTRACT

Both apparatus and the method is directed to a sampler array carrying a plurality of samplers in which the array has a trip assembly with a plurality of lanyard release pins. One moving member in the assembly contains a pivotal cam which is spring loaded in order to pass a plurality of lanyard release pins in one direction, but to move in the opposite direction and depress the lanyard release pin thereby releasing the lanyard to a preselected sampler for purposes of closing the same and entrapping a sample by the exact sampler desired by the operator at the surface. The method then contemplates counting the degrees of movement of a moving trip wheel having a release cam in one direction in which each sampler lanyard release pin is bypassed, and thereafter reversing the same having the lanyard release pin which is desired to be activated confronts the angled under surface of the lanyard release cam which, when reversed, will depress the lanyard release pin and release the lanyard to close the sampler.

5 Claims, 4 Drawing Sheets

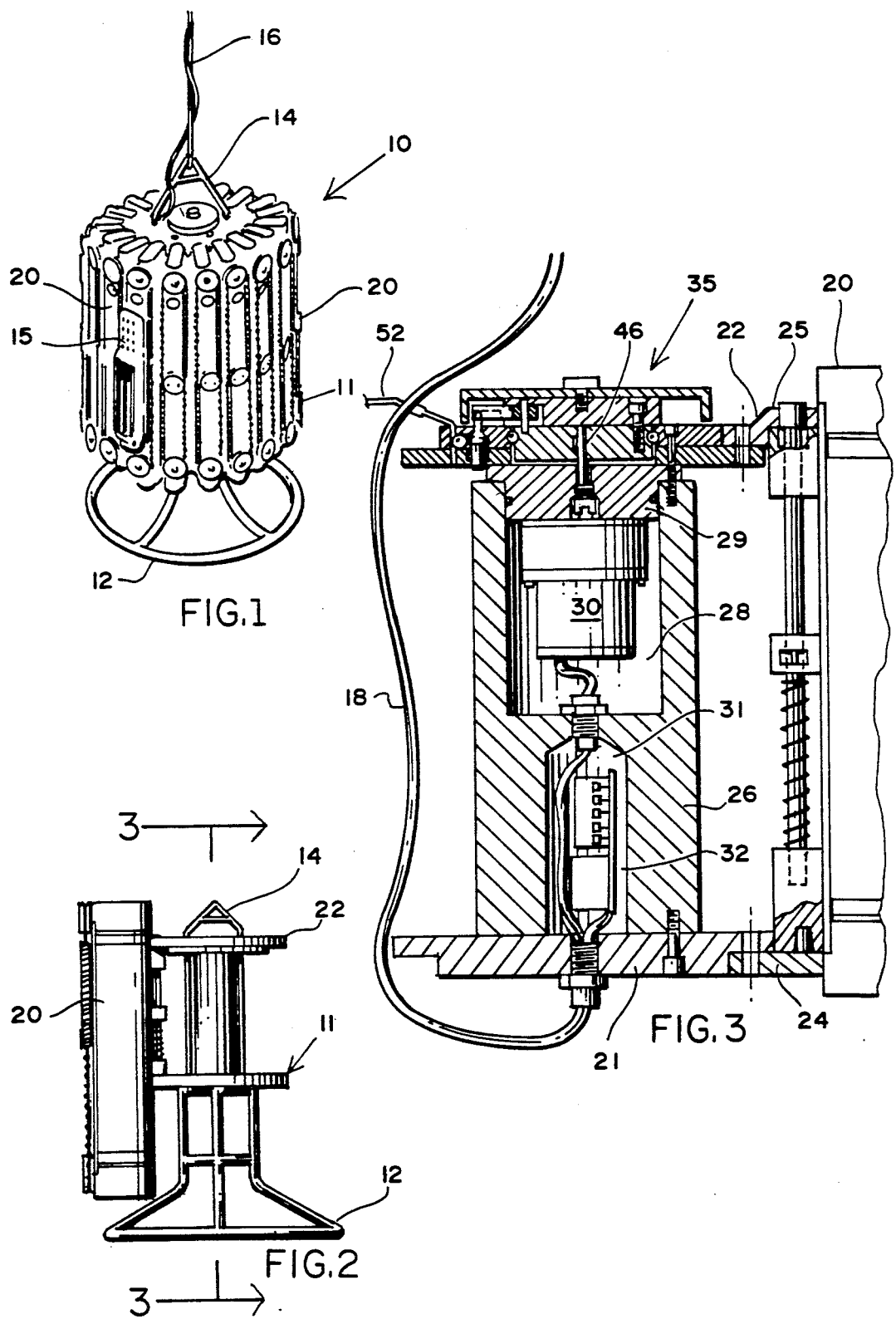

MULTIPLE SAMPLER ARRAY AND A METHOD

FIELD OF THE INVENTION

The present invention relates to a multiple sampler array used primarily for sampling ocean water at preselected depths generally as illustrated by U.S. Pat. No. 4,037,477 and copending patent application Ser. No. 532,444, filed Jun. 4, 1990. The invention is directed to electing which of a multiple of samplers on an array is to be closed for purposes of taking a sample at any given depth.

SUMMARY OF THE PRIOR ART

Samplers for sampling ocean water, fresh water, and other fluids are known and have been used for years. They are exemplified in U.S. Pat. No. 4,037,477 now the property of the assignee of this patent application. In the subject patent entitled "Water Sampler Device" additional prior art, seven U.S. patents in number and one British patent have been made a matter of record. The device of U.S. Pat. No. 4,037,477 includes, primarily, an elongated tubular member or bottle 11 having a chamber 12 which is adapted to collect and retain a water sample. Such devices have functioned successfully over the years and are currently in use.

Other examples of the prior art, irrespective of whether shown in issued patents, or known by their tradename are the following: For example, patents owned by the applicants' assignee relating to samplers include U./S. Pat. Nos. 3,242,740; 3,425,664; 3,489,012; 3,815,422; 3,986,635; 4,037,477; 4,091,676; 4,106,751; 4,302,974; 4,347,751; 4,593,570; 4,744,256 and 4,852,413. In addition, TRW Patent 3,866,474; J. D. Richard U.S. Pat. No. 3,367,191; and Scott Gowing Patent assigned to the United States Navy, U.S. Pat. No. 4,635,487 also relates to water samplers. Finally, not in the patent literature, is the product being offered by Falmouth Scientific, Inc. of North Falmouth, Mass. under the trademark "Aqua Pure" sampling system.

Such samplers may be mounted in an array, and the entire array is submersed. The array can then be activated so that all of the samplers are open. A program driven motor which is driven from the surface will sequentially and serially close various ones of the sampler. If there are twelve samplers, you first close No. 1, you second close No. 2, etc. None are skipped unless a sampler is missing from the array. There are occasions, more often than one might expect, when different ones of the samplers may be of different sizes, or adapted for different types of sampling, when it is highly desirable to be able to elect which sampler to close. For example, it might be that sampler No. 3 would be the first to be closed as the array descends because of certain of its characteristics. Thereafter, once reaching a further depth, it might be desirable to close sampler No. 9. Following No. 9, because of a temperature reading or other intelligence transmitted to the surface, it might be that sampler No. 2 should be closed, and then sampler No. 1, followed by 7 or 8. With the present state of the art, this controlled sequencing cannot be achieved. It is, therefore, highly desirable to develop an array with a plurality of samplers and have the capability of samples to be taken while the array is under the surface.

SUMMARY OF THE INVENTION

The present invention, both apparatus and method, is directed to a sampler array carrying a plurality of samplers in which the array has a trip assembly with a plurality of lanyard release pins. One moving member in the assembly contains a pivotal cam which is spring loaded in order to pass a plurality of lanyard release pins in one direction, but to move in the opposite direction and depress the lanyard release pin thereby releasing the lanyard to a preselected sampler for purposes of closing the same and entrapping a sample by the exact sampler desired by the operator at the surface. The method then contemplates measuring the extent of movement of a moving trip wheel having a release cam in one direction in which each sampler lanyard release pin is bypassed, and thereafter reversing the same having the lanyard release pin which is desired to be activated engage the pivotal cam which depresses the lanyard release pin and release the lanyard to close the sampler.

In view of the foregoing it is a principal object of the present invention to provide an apparatus and method for preselecting from an array of samplers which is primarily intended for underwater sampling and providing control means which will permit the operator at the surface to trap a sample from any given one of the samplers at any given time.

A further object of the present invention is to provide a sampler with the elective feature as set forth above, which is compatible with pre-existing samplers and samplers of a wide variety of configurations, material, and selectivity as to depth and content.

Yet another object of the present invention is to provide the above features in a sampler array which is cost-effective when contrasted with state-of-the-art sampler arrays.

BRIEF DESCRIPTION OF THE DRAWINGS

Further objects and advantages of the present invention will become apparent as the following description of an illustrative embodiment takes place, as set forth in the accompanying illustrative drawings, in which:

FIG. 1 is a perspective view of a sampler array illustrative of the present invention;

FIG. 2 is a front elevation of an array showing one sampler in position and illustrative of the present invention;

FIG. 3 is a Cutaway View of the sampler array of FIG. 2 but showing a different sampler location;

DESCRIPTION OF A PREFERRED EMBODIMENT

Figure 4:
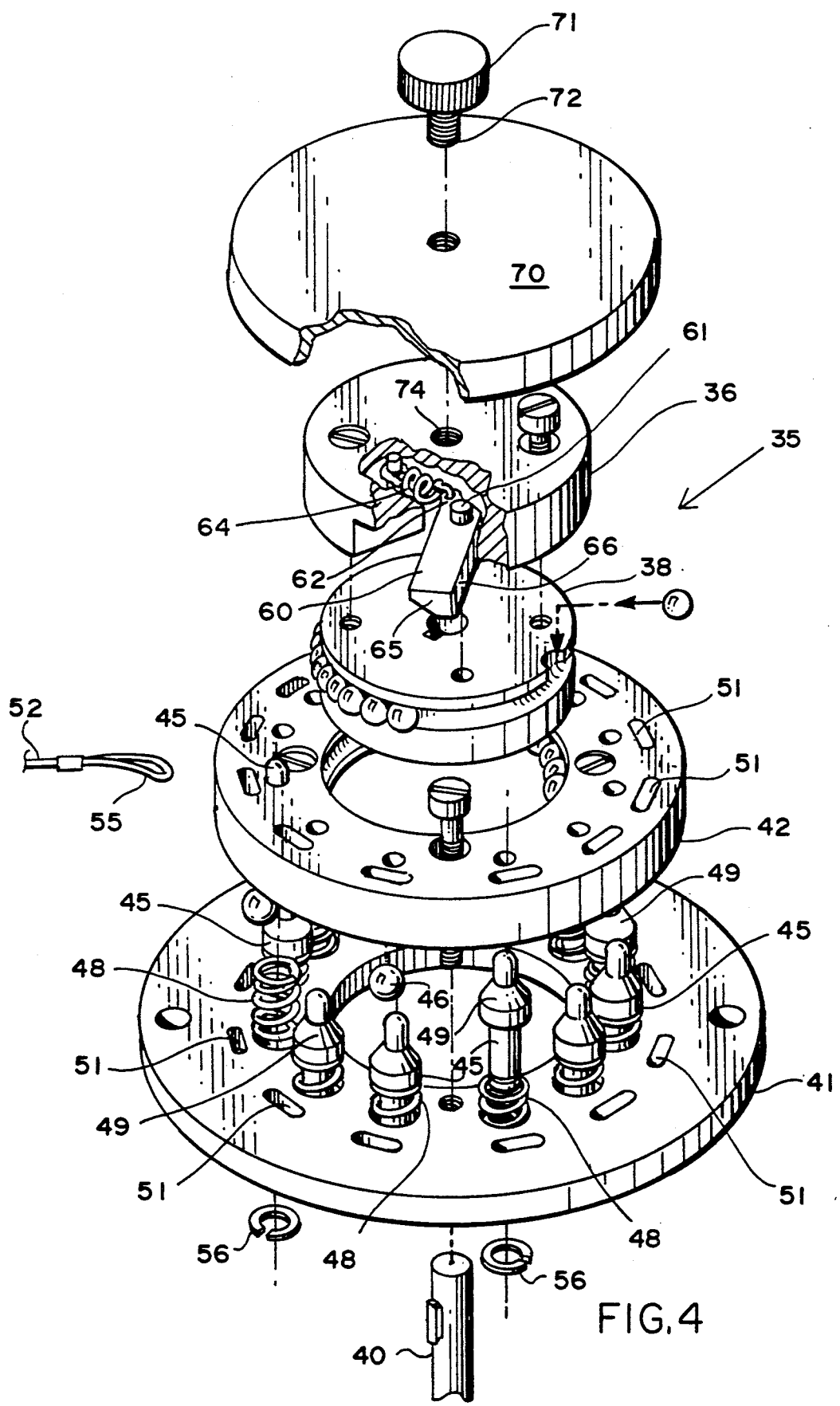
FIG. 4 is a perspective exploded view of the trip assembly of the subject array illustrating the trip assembly, trip arm, driving means, and control circuit in their relative relationship each to the other.
Figure 5:
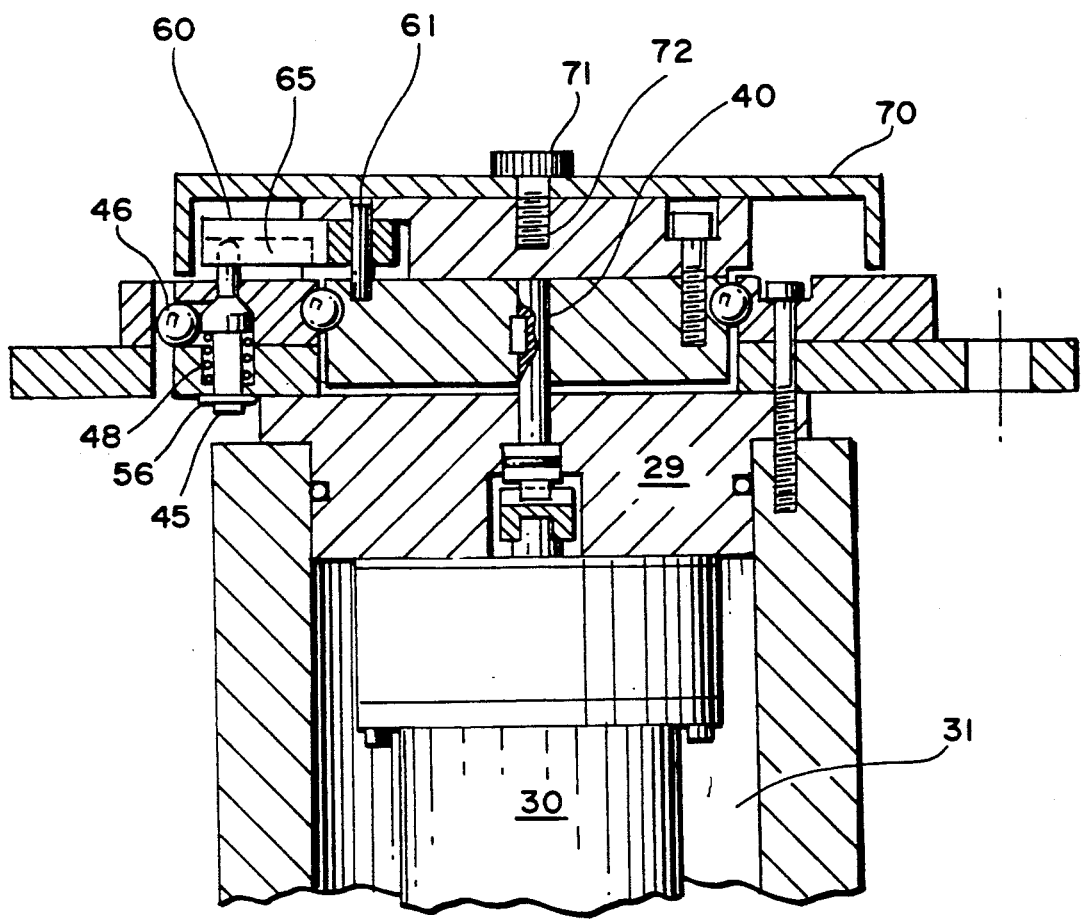
FIG. 5 is an enlarged cutaway view of the trip assembly at the upper portion of the sampler array shown in cutaway view in reduced scale in FIG. 3.

The present invention is illustrated in the embodiment of a sampler array 10 as shown in FIG. 1. There it will be seen that the sampler array 10 is mounted in a stand 11 having a circular foot 12. A hanger 14 extends from the upper portion of the stand and a support cable 16 is secured to the hanger 14. Samplers 20 are grouped in a circular fashion between the upper and lower support assembly 21, 22 as shown in FIG. 1, and a reverse thermometer 15 is mounted at a preselected position on the exterior of the sampler array 10.

As illustrated in FIG. 2, the sampler array 11 and its stand 12 coupled with the hanger 14 permit the attachment of a plurality of samplers 20, only one being shown in FIG. 2. FIG. 3 which is a cutaway somewhat enlarged from that shown in FIG. 2 with the sampler 20 shown at a different location, includes a lower support ring 21 and an upper support ring 22 with lower sampler mounts 24 and upper sampler mounts 25 for securing the samplers 20 in place.

A central pylon body 26 essentially spans the place between the lower support ring and upper support rings 21, 22. A motor well 28 is provided in the upper portion of the pylon body 26 and the upper end is closed by means of the motor cup 29 which is secured to the pylon body 26. The motor 30 is mounted above a control well 31 in which a plurality of electronic controls 32 are provided. These controls are coupled by means of drive cable 18 to the operator at the surface, and also include the power means for the step motor 30. Desirably a step motor is employed, but other drive sources which can be selectively positioned will also achieve the desired results.

At the upper portion of the pylon body 26 a trip assembly 35 is provided which includes a trip wheel 36 (see FIG. 4) and a trip wheel drive 38. A drive shaft 40 couples the motor 30 to the trip wheel 36 and its mount 38. Lower release plate 41 and upper release plate 42 serve as a mount for the release pins 45 and the release balls 46. Each one of the release pins 45 is biassed by means of a release pin spring 48 to hold the upper portion of the release pin in the upper condition of mounting. The release pin head 50 is separated from the body portion of the release pin 45 by means of a release pin taper 49.

Figure 8:
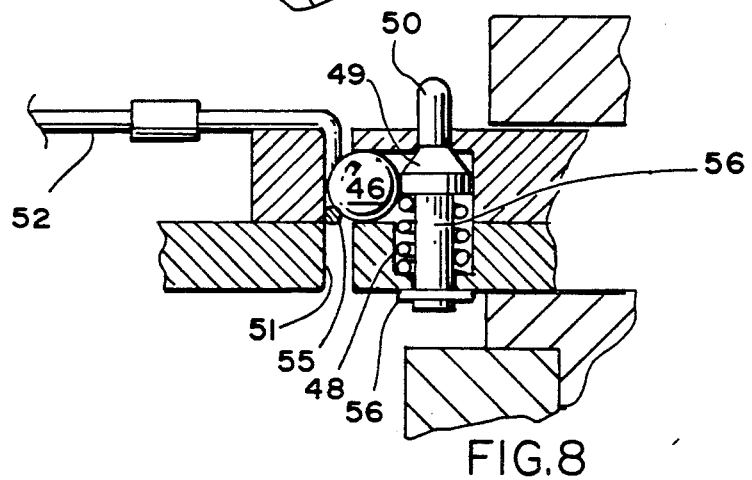
FIG. 8 is an enlarged cutaway partially broken and showing the relationship between the release pin and the release ball when the lanyard loop is in the locked position.

The lanyard 52 and its lanyard loop 55 are secured in the lanyard slots 51 as best shown in FIG. 8. The loop is depressed into the lanyard slots 51 when the release pin head 50 is depressed and the release ball 46 rolls away from the lanyard slot 51. Once the lanyard loop 55 is beneath the position of the release ball 46, the release pin 45 is permitted to move upwardly and its main body portion engages the release ball 46, as shown in FIG. 8, to lock the lanyard loop 55 in its secured position. At this point the sampler 20 is awaiting the release of the lanyard 52 which will close the sampler 20. A spring anchor 56 is provided for the release pin spring 48 to secure the same urging the release pin head 50 to the upward position at which time the release ball 46 locks the lanyard loop 55.

Figure 6:
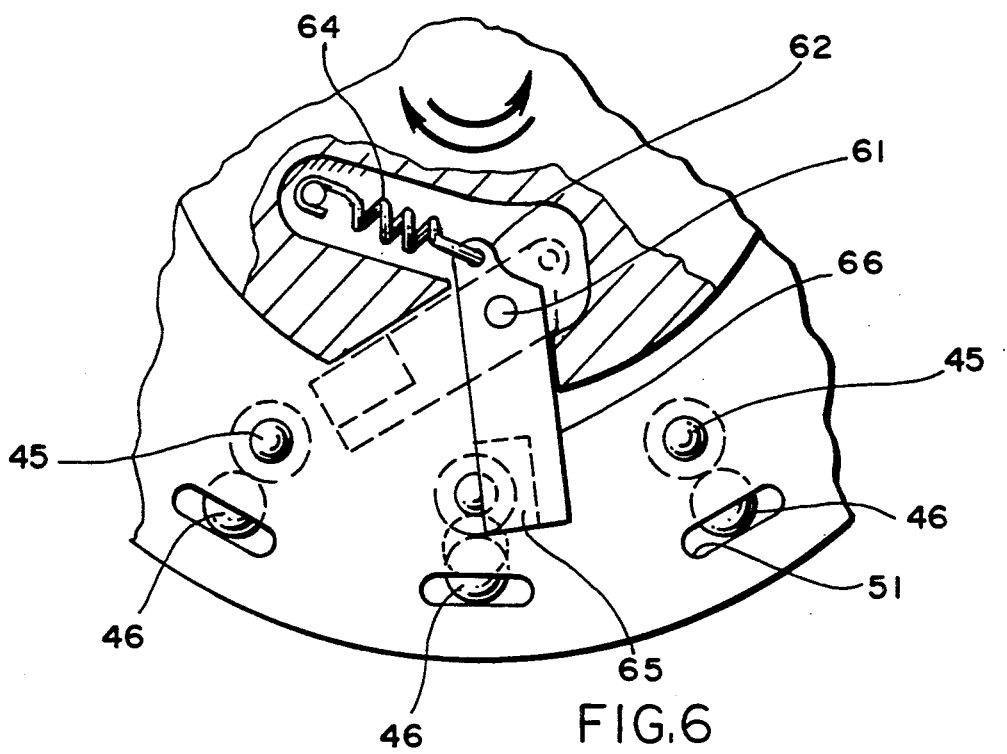
FIG. 6 is a top elevation partially broken of the trip arm and its relationship to the trip assembly.
Figure 7:
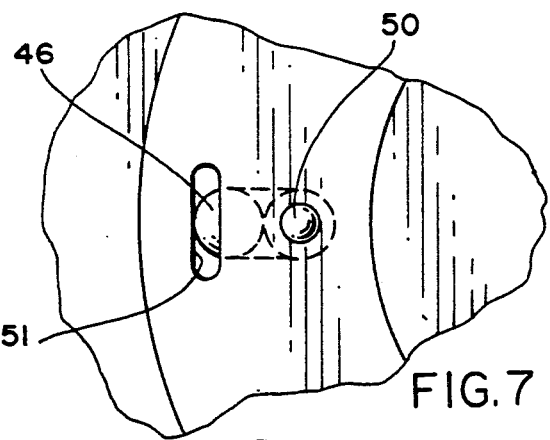
FIG. 7 is a broken view showing the relationship between the release pin head and the release ball.
Figures 9, 10:
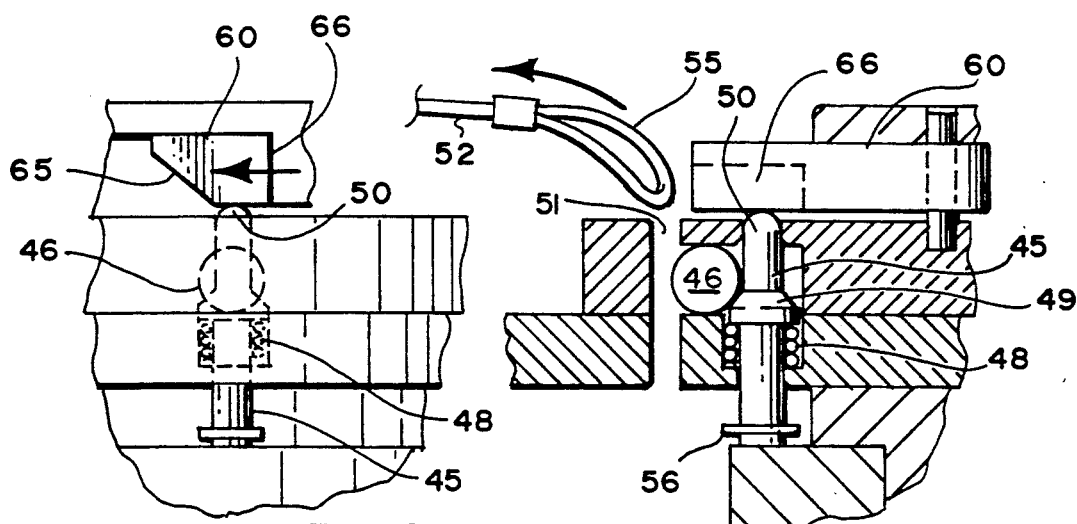
FIG. 9 is an end view of the trip arm showing how its cammed face depresses the release pin.
FIG. 10 is a view comparable to that shown in FIG. 8 but illustrating how the lanyard and the lanyard loop are released from the release ball when the trip pin is lowered when engaged by the cam face of the trip arm.

Turning now to FIG. 6, it will be seen that the trip arm 60 is pivotally mounted on trip arm pivot 61 and spring mount extension 62 is secured to a pivot spring 64. In this fashion when the trip wheel 38 is rotated in a counterclockwise fashion as shown in FIG. 6, the trip arm 60 will pivot to the position as shown in phantom lines. This occurs repetitively each time the trip arm 60 engages the pin head 50 with its skip face 66. When it is desired to release a lanyard 52, the rotation of the trip wheel 38 is reversed, and then (as best shown in FIG. 9) the cam 65 of the trip arm 60 which is at an angle, engages the release pin head 50 which works against the release spring pin 48 to move into the position as shown in FIG. 10 whereupon the lanyard loop 55 is released from the release ball 46 and the lanyard loop 55 disengages from the release ball 46 and the power spring on the sampler, the lanyard once released, closes the sampler.

The trip wheel 36 and the trip wheel drive 38 are also secured including the lower release plate 41 and upper release plate 42 by means of trip assembly cover 70 (shown in exploded relationship in FIG. 4) which is secured by means of the cover mount 71 having a downwardly depending threaded mounting shank 72, when the same is threaded into the mount bore 74 in the trip wheel 36.

The method of the invention contemplates the steps of, through a control circuit 32 such as illustrated, counting the release pins passed by means of the trip arm skip face 66 to positively at all times know the space between adjacent release pins 45. Once the trip arm has passed the sampler which is to be closed, the method is directed to determining the position of the trip arm with regard to its two adjacent sampler pins 50, and then reversing the trip wheel 36 to cause the cam face 65 of the trip arm 60 to depress the release pin 45 of the release pin just passed, and counting the position to reference the sampler just released as having been closed, and retaining in memory the identification of the release pins which have not been released and continue to lock their respective lanyard 52 through its lanyard loop 55. The sequence is repeated until the desired number of samplers 20 have been closed. A permanent memory is desirably kept of the sequence in which the samplers were closed and if chosen, the relevant depth when closed, the relevant temperature when closed, and any other information which is sensed at the time the particular sampler is closed.

It will be understood that various changes in the details, materials and arrangements of parts which have been herein described and illustrated in order to explain the nature of the invention, may be made by those skilled in the art within the principle and scope of the invention as expressed in the appended claims.

What is claimed is:

1. A sampler array comprising an array for holding a plurality of samplers, each sampler having a lanyard holding it open when said lanyard is stretched,
   said sampler array having a trip assembly with a fixed member and a moving member,
   means for driving the moving member to programmable positions,
   said fixed member having lanyard engaging means for removably securing a plurality of closing lanyards for the samplers secured to the array,
   said moving member having a pivotal trip arm for releasing selective ones of said lanyards depending upon the direction of moving of the moving member,
   said trip arm being pivotally constrained for rotation in one direction to continuously pass the lanyard engaging means and yet upon reversal to engage and deactivate the lanyard engaging means thereby preselectively releasing said lanyards in accordance with the position immediately prior to reversal.

2. In the sampler array of claim 1 above,
said pivotal trip arm being pivotally secured by a spring permitting the same pivot when moving in one direction, and restrict pivoting when moving in the other direction.

3. In the sampler array of claim 2 above,
said trip arm having a cam face and a trip face at the end remote from the pivot spring,
said lanyard engaging means comprising spring loaded pins, a release ball, and a lanyard slot,
said cam face being angled to engage a trip pin when rotated in one direction, and said trip face being pivotally and yieldably mounted to skip the pin when moved in an opposite direction.

4. In the sampler array of any of claims 1, 2, or 3 in which:
said moving member is a rotary head.

5. A multiple sampler having means for programming and operating in which said sampler has a fixed head and a moving head, the moving head containing a pivotal cam member which can engage lanyard engaging means in one direction, but bypass them in another, and a fixed member having lanyard engaging means which are coupled to a sampler array and configured to release the closing lanyard upon engagement by cam, and;
means for preselecting a position within the release cam in a predetermined relationship too each of the lanyard engaging means,
means for moving the moving head until the release cam passes the lanyard engaging means to be disengaged,
means for reversing the moving head from a position between the lanyard to be disengaged and disengaging the same to a position adjacent to the next lanyard engaging means,
and means for recording the extended movement of the moving head past any of the lanyard engaging means,
whereby the moving head may be moved for as many positions as there are lanyard engaging means, and thereafter reversed to disengage a predetermined lanyard thereby closing the preselected sampler desired at that given time.

* * * * *